US000002019H

(19) United States

(12) Statutory Invention Registration

Skatrud et al.

(10) Reg. No.: US H2019 H

(43) Published: Apr. 2, 2002

(54) *STREPTOCOCCUS PNEUMONIAE* GENE SEQUENCE HI1648

(76) Inventors: Paul Luther Skatrud, Greenwood; Robert Brown Peery, Brownsburg; Patti Jean Treadway, Greenwood, all of IN (US)

(21) Appl. No.: 09/198,284

(22) Filed: Nov. 23, 1998

Related U.S. Application Data

(62) Division of application No. 08/987,122, filed on Dec. 8, 1997.

(60) Provisional application No. 60/036,281, filed on Dec. 13, 1996.

(51) Int. Cl.[7] ..... C07H 19/00

(52) U.S. Cl. ..... 536/22.1; 435/6

(58) Field of Search ..... 435/6; 536/22.1; 530/350

(56) References Cited

PUBLICATIONS

Fleischmann, et al. "Whole–Genome Random Sequencing and Assembly of *Haemophilus influenzae* Rd." *Science* 269:496–512 (Jul. 28, 1995).

*Primary Examiner*—Eggerton A. Campbell

(57) ABSTRACT

The invention provides isolated nucleic acid compounds encoding HI1648 of *Streptococcus pneumoniae*. Also provided are vectors and transformed host cells for expressing the encoded protein, and a method for identifying compounds that bind and/or inhibit said protein.

2 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

*STREPTOCOCCUS PNEUMONIAE* GENE SEQUENCE HI1648

This application claims the benefit of divisional of Ser. No. 08/987,122, filed on Dec. 8, 1997 U.S. Provisional Application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptccoccus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae.*

BRIEF SUMMARY OF THE INVENTION

The present invention relates to an isolated gene and encoded protein from *S. pneumoniae.* The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding HI1648 protein.

In another embodiment, the invention relates to a nucleic acid molecule comprising the nucleotide sequence identified as SEQ ID NO:1 or SEQ ID NO:3.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the HI1648 gene in operable linkage to gene expression sequences enabling the gene to be transcribed and translated in a host cell.

In still another embodiment the present invention relates to host cells that have been transformed or transfected with the cloned HI1648 gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the HI1648 protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature "Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae.* The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the string ency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° C. in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of $NaH_2PO_4.H_2O$, and 7.4 g of EDTA in 800 ml of $H_2O$. The pH is adjusted with NaOH and the volume brought to 1 liter.

"SSC" denotes. a hybridization and wash solution comprising sodium chloride and sodium citrate at pH 7. A 20× solution of SSC is made by dissolving 175 g of NaCl and 88 g of sodium citrate in 800 ml of $H_2O$. The volume is brought to 1 liter after adjusting the pH with 10N NaOH.

The HI1648 gene disclosed herein (SEQ ID NO:1) and related nucleic acids (e.g. SEQ ID NO:3 and SEQ ID NO:4) encode a protein of unknown function. Since knockout mutations of the HI1648 gene produce a loss in viability, the 1648 protein product may be essential for viability.

The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application,* Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology,* 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach,* (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, N.Y., 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the *Escherichia coli* K12 strain 294 (ATCC No. 31446) is particularly useful for expression of foreign proteins.

Other strains of *E. coli,* bacilli such as *Bacillus subtilis,* enterobacteriaceae such as *Salmonella typhimurium* or *Serratia marcescans,* various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b-lactamase [e.g. vector pGX2907, ATCC 39344, contains a replicon and b-lactamase gene], lactose systems [Chang et al., *Nature* (London), 275:615. (1978); Goeddel et al., *Nature* (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis,* are also suitable. For expression of recombinant genes in Saccharomyces, the plasmid YRp7 (ATCC-40053), for example, may be used. See, e.g., L. Stinchcomb, et al., *Nature,* 282:39 (1979); J. Kingsman et al., *Gene,* 7:141 (1979); S. Tschemper et al., *Gene,* 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," *In Methods in Enzymology,* Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. In a preferred method, a radioactively-labeled or. chemically-labeled compound or protein is used. A specific association between the test compound and protein is monitored by any suitable means.

In such a screening protocol HI1648 is prepared as described herein, preferably using recombinant DNA technology. A test compound is introduced into a reaction vessel containing the HI1648 protein or fragment thereof. Binding of HI1648 by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a HI1648 protein, perhaps as a lead to a pharmaceutical compound for modulating the state of differentiation of an appropriate tissue. A ligand that binds HI1648, or related fragment thereof, is identified, for example, by combining a test ligand with HI1648 under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperoning protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* HI1648 in a Host Cell

An expression vector suitable for expressing *S. pneumoniae* HI1648 in a variety of procaryotic host cells, such as *E. coli,* is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the HI1648 coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* HI1648 (SEQ ID NO:1). The coding region for HI1648 is easily produced by PCR technology using suitably designed primers to the ends of the coding region specified in SEQ ID NO:1.

The HI1648 encoding nucleic acid used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by *S. pneumoniae* HI1648

An expression vector that carries HI1648 from the *S. pneumoniae* genome as disclosed herein and which H11648 is operably-linked to an expression promoter is transformed into *E. coli* BL21 (DE3) (hsdS gal lcIts857 ind1Sam7nin5lacUV5-T7 gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 5 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
(A) LENGTH: 579 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1..579

(xi) SEQUENCE DESCRIPTION: SEQ ID NO: 1:

```
ATG AAA ATC GGA ATA TTG GCC TTG CAA GGG GCC TTT GCA GAA CAT GCA       48
Met Lys Ile Gly Ile Leu Ala Leu Gln Gly Ala Phe Ala Glu His Ala
  1               5                  10                  15

AAA GTG CTA GAT CAA TTA GGT GTC GAG AGT GTA GAA CTC AGA AAT CTA       96
Lys Val Leu Asp Gln Leu Gly Val Glu Ser Val Glu Leu Arg Asn Leu
             20                  25                  30

GAT GAT TTT CAG CAA GAT CAG AGT GAC TTG TCG GGT TTG ATT TTG CCT      144
Asp Asp Phe Gln Gln Asp Gln Ser Asp Leu Ser Gly Leu Ile Leu Pro
         35                  40                  45

GGT GGT GAG TCT ACA ACC ATG GGC AAG CTC TTA CGT GAC CAG AAC ATG      192
Gly Gly Glu Ser Thr Thr Met Gly Lys Leu Leu Arg Asp Gln Asn Met
     50                  55                  60

CTA CTT CCC ATA CGA GAA GCC ATT CTA TCT GGC TTA CCA GTG TTT GGG      240
Leu Leu Pro Ile Arg Glu Ala Ile Leu Ser Gly Leu Pro Val Phe Gly
 65                  70                  75                  80

ACC TGT GCG GGC TTA ATT TTG CTG GCT AAG GAA ATC ACT TCT CAG AAA      288
Thr Cys Ala Gly Leu Ile Leu Leu Ala Lys Glu Ile Thr Ser Gln Lys
                 85                  90                  95

GAG AGT CAT CTA GGA ACT ATG GAT ATG GTG GTC GAG CGT AAT GCT TAT      336
Glu Ser His Leu Gly Thr Met Asp Met Val Val Glu Arg Asn Ala Tyr
            100                 105                 110

GGG CGC CAA TTA GGA AGT TTC TAC ACG GAA GCA GAA TGT AAG GGA GTT      384
Gly Arg Gln Leu Gly Ser Phe Tyr Thr Glu Ala Glu Cys Lys Gly Val
        115                 120                 125

GGC AAG ATT CCA ATG ACC TTT ATC CGT GGT CCG ATT ATC AGT AGT GTT      432
Gly Lys Ile Pro Met Thr Phe Ile Arg Gly Pro Ile Ile Ser Ser Val
    130                 135                 140

GGT GAG GGT GTA GAA ATT TTA GCA ATA GTG AAC AAT CAA ATT GTT GCA      480
Gly Glu Gly Val Glu Ile Leu Ala Ile Val Asn Asn Gln Ile Val Ala
145                 150                 155                 160

GCC CAA GAA AAA AAT ATG TTG GTA AGT TCT TTT CAT CCA GAA TTG ACT      528
Ala Gln Glu Lys Asn Met Leu Val Ser Ser Phe His Pro Glu Leu Thr
                165                 170                 175

GAT GAT GTG CGC TTG CAC CAG TAC TTT ATC AAT ATG TGT AAA GAA AAA      576
Asp Asp Val Arg Leu His Gln Tyr Phe Ile Asn Met Cys Lys Glu Lys
            180                 185                 190

AGT                                                                  579
Ser
```

-continued (2) INFORMATION FOR SEQ ID NO: 2:

(i) SEQUENCE CHARACTERISTICS:
(A) LENGTH: 193 amino acids
(B) TYPE: amino acid
(D) TOPOLOGY: linear (ii) MOLECULE TYPE: protein (xi) SEQUENCE DESCRIPTION: SEQ ID NO: 2:

```
Met Lys Ile Gly Ile Leu Ala Leu Gln Gly Ala Phe Ala Glu His Ala
  1               5                  10                  15

Lys Val Leu Asp Gln Leu Gly Val Glu Ser Val Glu Leu Arg Asn Leu
             20                  25                  30

Asp Asp Phe Gln Gln Asp Gln Ser Asp Leu Ser Gly Leu Ile Leu Pro
         35                  40                  45

Gly Gly Glu Ser Thr Thr Met Gly Lys Leu Leu Arg Asp Gln Asn Met
     50                  55                  60

Leu Leu Pro Ile Arg Glu Ala Ile Leu Ser Gly Leu Pro Val Phe Gly
 65                  70                  75                  80

Thr Cys Ala Gly Leu Ile Leu Leu Ala Lys Glu Ile Thr Ser Gln Lys
                 85                  90                  95

Glu Ser His Leu Gly Thr Met Asp Met Val Val Glu Arg Asn Ala Tyr
            100                 105                 110

Gly Arg Gln Leu Gly Ser Phe Tyr Thr Glu Ala Glu Cys Lys Gly Val
        115                 120                 125

Gly Lys Ile Pro Met Thr Phe Ile Arg Gly Pro Ile Ile Ser Ser Val
    130                 135                 140

Gly Glu Gly Val Glu Ile Leu Ala Ile Val Asn Asn Gln Ile Val Ala
145                 150                 155                 160

Ala Gln Glu Lys Asn Met Leu Val Ser Ser Phe His Pro Glu Leu Thr
                165                 170                 175

Asp Asp Val Arg Leu His Gln Tyr Phe Ile Asn Met Cys Lys Glu Lys
            180                 185                 190

Ser
```

(2) INFORMATION FOR SEQ ID NO: 3:

(i) SEQUENCE CHARACTERISTICS:
(A) LENGTH: 579 base pairs
(B) TYPE: nucleic acid
(C) STRANDEDNESS: single
(D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO: 3:

```
AUGAAAAUCG GAAUAUUGGC CUUGCAAGGG GCCUUUGCAG AACAUGCAAA AGUGCUAGAU     60

CAAUUAGGUG UCGAGAGUGU AGAACUCAGA AAUCUAGAUG AUUUUCAGCA AGAUCAGAGU    120

GACUUGUCGG GUUUGAUUUU GCCUGGUGGU GAGUCUACAA CCAUGGGCAA GCUCUUACGU    180

GACCAGAACA UGCUACUUCC CAUACGAGAA GCCAUUCUAU CUGGCUUACC AGUGUUUGGG    240

ACCUGUGCGG GCUUAAUUUU GCUGGCUAAG GAAAUCACUU CUCAGAAAGA GAGUCAUCUA    300

GGAACUAUGG AUAUGGUGGU CGAGCGUAAU GCUUAUGGGC GCCAAUUAGG AAGUUUCUAC    360
```

-continued

```
ACGGAAGCAG AAUGUAAGGG AGUUGGCAAG AUUCCAAUGA CCUUUAUCCG UGGUCCGAUU    420

AUCAGUAGUG UUGGUGAGGG UGUAGAAAUU UUAGCAAUAG UGAACAAUCA AAUUGUUGCA    480

GCCCAAGAAA AAAAUAUGUU GGUAAGUUCU UUUCAUCCAG AAUUGACUGA UGAUGUGCGC    540

UUGCACCAGU ACUUUAUCAA UAUGUGUAAA GAAAAAAGU                           579
```

(2) INFORMATION FOR SEQ ID NO: 4:

(i) SEQUENCE CHARACTERISTICS:
(A) LENGTH: 1863 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

```
GAGCTCGGTA CCCGGGGATC ATACTCAAGA GGAGGTAATC CAATGAACAC TAGTCTTAAA     60

CTCAGCAAAC AACTCAGTTT TGGAGAGGAG ATTGCTAATA GCGTGACCCA TGCTGTGGGT    120

GCAGTCATCA TGCTTATCTT GCTGCCTATT TCATCCATCT ATAGTTATGA AGCACACGGA    180

TTTTTATCCT CTATCGGCGT TTCCATTTTC GTCATCAGTC TCTTTCTCAT GTTCCTATCA    240

TCCACCATTT ATCACTCTAT GGCCTATGGT TCGACCCACA AATATGTTTT GCGAATCATT    300

GACCATTCTA TGATTTACGT TGCCATTGCC GGCTCATACA CGCCCGTTGT CTTGACCTTG    360

ATGAATAACT GGTTTGGCTA TCTGATTATT GTCATCCAAT GGGGAACGAC CATCTTTGGT    420

ATTCTCTATA AAATCTTTGC TAAAAAGGTC AATGAGAAAT TTAGCCTTGC TCTTTACCTG    480

ATTATGGGCT GGTTGGTTCT GGCTATCATT CCTGCCATTA TCAGTCAAAC GACACCCGTT    540

TTCTGGAGTC TCATGGTAAC TGGCGGACTC TGTTATACAG TTGGAGCTGG ATTTTATGCC    600

AAGAAAAAAC CTTATTTCCA CATGATTTGG CATCTCTTTA TCCTAGCTGC GTCCGCACTC    660

CAATACATCG CTATTGTTTA TTACATGTAA AAAAGTTGAG AAATTCAATC TCAACTTTTT    720

TCTTTACACA TATTGATAAA GTACTGGTGC AAGCGCACAT CATCAGTCAA TTCTGGATGA    780

AAAGAACTTA CCAACATATT TTTTTCTTGG GCTGCAACAA TTTGATTGTT CACTATTGCT    840

AAAATTTCTA CACCCTCACC AACACTACTG ATAATCGGAC CACGGATAAA GGTCATTGGA    900

ATCTTGCCAA CTCCCTTACA TTCTGCTTCC GTGTAGAAAC TTCCTAATTG GCGCCCATAA    960

GCATTACGCT CGACCACCAT ATCCATAGTT CCTAGATGAC TCTCTTTCTG AGAAGTGATT   1020

TCCTTAGCCA GCAAAATTAA GCCCGCACAG GTCCCAAACA CTGGTAAGCC AGATAGAATG   1080

GCTTCTCGTA TGGGAAGTAG CATGTTCTGG TCACGTAAGA GCTTGCCCAT GGTTGTAGAC   1140

TCACCACCAG GCAAAATAAA CCCGACAAGT CACTCTGATC TTGCTGAAAA CATCTAGATT   1200

TCTGAGTTCT ACACTCTCGA CACCTAATTG ATCTAGCACT TTTGCATGTT CTGCAAAGGC   1260

CCCTTGCAAG GCCAATATTC CGATTTTCAT CTATTTTCCT CGTTCAGCCA TGAGAATTTG   1320

GATTCATTTT CATTAATACC AACCATGGCT TCTCCTAAAT CTTCAGAGAT TTGAGCTAGG   1380

ATTTGAGGAT TACGGAAGTT AGTCACAGCC TTAACAATGG CACTCGCTCG TTTAACAGGA   1440

TCTCCTGACT TGAAAATACC TGAACCGACA AAGACCCCCT CTGCCCCTAA TTGCATCATT   1500

AACGCAGCAT CTGCTGGCGT TGCAACACCT CCAGCAGCGA AATTTACAAC TGGCAATTTT   1560

CCATGTTCAT GAACATATTG GACCAATTCT ACAGGGACTT GCAAATCCTT GGCAGCAACA   1620
```

-continued

```
TAAAGCTCGT CCTCACGTAA GTTTTGAATG CGGCGAATTT CCTGATTCAT CATACGCATA   1680
TGACGAACAG CTTGGACTAT ATCCCCTGTC CCTGGTTCTC CTTTAGTACG AATCATGGAA   1740
GCACCTTCAG CGATACGACG CAAGGCTTCA CCCAAATCCT TAGCACCACA GACAAAAGGA   1800
ACTTGGAATT CTTTCTTGTC CACATGGAAA CGGTCATCAG CTGGAGATAG AACTTCACTC   1860
TCG                                                                 1863
```

We claim:

1. An isolated protein having the amino acid sequence shown in SEQ ID NO:2.

2. A method for identifying compounds that bind a protein identified herein as SEQ ID NO:2, comprising the steps of:

a) admixing a substantially purified preparation of a protein comprising SEQ ID:2 with a test compound; and b) monitoring by any suitable means a binding interaction between said protein and said compound.

* * * * *